United States Patent [19]
Steiger et al.

[11] Patent Number: 5,243,855
[45] Date of Patent: Sep. 14, 1993

[54] APPARATUSES AND METHODS FOR MEASURING ULTRASONIC VELOCITIES IN MATERIALS

[75] Inventors: Ronald P. Steiger, Houston; Peter K. Leung, Sugar Land, both of Tex.

[73] Assignee: Exxon Production Research Company, Houston, Tex.

[21] Appl. No.: 576,697

[22] Filed: Aug. 31, 1990

[51] Int. Cl.$^5$ .............................................. E21B 49/02
[52] U.S. Cl. ......................................... 73/153; 73/38; 73/151; 166/250
[58] Field of Search ................ 166/250; 73/38, 152, 73/153, 151, 594

[56] References Cited

U.S. PATENT DOCUMENTS

| | | | |
|---|---|---|---|
| 2,634,613 | 4/1953 | Napier | 73/38 |
| 2,703,977 | 3/1955 | Bailly | 73/38 |
| 2,705,418 | 4/1955 | Reichertz et al. | 73/38 |
| 2,737,804 | 3/1956 | Herzog et al. | 73/38 |
| 3,139,747 | 7/1964 | Ferrell et al. | 73/38 |
| 3,199,341 | 8/1965 | Heuer, Jr. et al. | 73/820 |
| 3,216,242 | 11/1965 | Eyrich | 73/38 |
| 3,313,151 | 4/1967 | Kaye | 73/562.65 |
| 3,421,366 | 1/1969 | Ely | 73/819 |
| 3,423,994 | 1/1969 | Scott et al. | 73/819 |
| 3,423,995 | 1/1989 | Scott et al. | 73/819 |
| 3,457,777 | 7/1969 | Nielsen | 73/84 |
| 3,505,860 | 4/1970 | Bishop et al. | 73/819 |
| 3,537,541 | 11/1970 | Desai | 73/594 |
| 3,610,032 | 10/1971 | Di Crispino | 73/819 |
| 3,616,685 | 11/1971 | Strom | 73/819 |
| 3,635,078 | 1/1972 | Wissa | 73/89 |

(List continued on next page.)

FOREIGN PATENT DOCUMENTS

| | | | |
|---|---|---|---|
| 0080534 | 5/1983 | Japan | 73/862.65 |
| 0252707 | 11/1968 | U.S.S.R. | 73/38 |
| 0794434 | 7/1981 | U.S.S.R. | 73/38 |

OTHER PUBLICATIONS

Lateral-deformation Gage for Rock-mechanics Testing by Karl W. Schuler (Experimental Mechanics) pp. 477-490, vol. 18 No. 12 (Dec. 1978).

"Quantitative Determination Of The Mechanical Properties Of Shales," Steiger and Leung, SPE Conference, Oct. 2-5, 1988.

"Predictions Of Wellbore Stability In Shale Formations At Great Depth," Steiger and Leung, SPE Symposium 1989.

"Acoustical Properties Of Clay Bearing Rocks," C. A. Tosaya, 1982.

"Drilling Fluids," Exxon Production Research Company, 1989.

"The Mechanics of Soils," Atkinson et al., 1978, pp. 118-144, 184-209, 292-343.

"Soil Mechanics," Lambe et al., 1969, Chapter 20, pp.295-303.

"Fundamentals Of Potassium Drilling Fluids: A Field Manual to Reduce Drilling and Completion Problems Associated with Hydratable Clays," Steiger, et al., 1985.

Primary Examiner—Hezron E. Williams
Assistant Examiner—George Dombroske
Attorney, Agent, or Firm—Guy McClung

[57] ABSTRACT

Methods and apparatuses are disclosed for determining a three factor envelope for the material of a preserved core sample. The three factors are ultrasonic velocity through the material, mean effective stress and an elastoplastic property of the material. Values are obtained, in one aspect of the invention, by applying a confining pressure to the material; measuring the material's pore pressure and the ultrasonic velocity therethrough; calculating the material's mean effective stress for that confining pressure; and then loading the sample to near shear failure to measure the value of the elastoplastic property. At different confining pressures the measurements are repeated on the same sample to obtain values for the mean effective stress and elastoplastic property at each level. The envelope is determined by graphically representing the data obtained.

8 Claims, 6 Drawing Sheets

U.S. PATENT DOCUMENTS

| | | | |
|---|---|---|---|
| 3,728,895 | 4/1973 | Shaw | 73/94 |
| 3,820,385 | 6/1974 | Cordoba | 73/84 |
| 3,881,345 | 5/1975 | Souder | 73/94 |
| 3,975,950 | 8/1976 | Erdei | 73/94 |
| 4,380,930 | 4/1983 | Podhrasky et al. | 73/594 |
| 4,430,890 | 2/1984 | Hains | 73/147 |
| 4,486,714 | 12/1984 | Davis et al. | 73/153 |
| 4,487,056 | 12/1984 | Wiley | 73/38 |
| 4,502,338 | 3/1985 | Smith et al. | 73/819 |
| 4,506,542 | 3/1985 | Rose | 73/38 |
| 4,561,289 | 12/1985 | Jones | 73/38 |
| 4,562,726 | 1/1986 | Barnaby | 73/38 |
| 4,566,311 | 1/1986 | Barnaby | 73/38 |
| 4,587,857 | 5/1986 | Bush | 73/863 |
| 4,599,891 | 7/1986 | Brauer et al. | 73/38 |
| 4,607,532 | 8/1986 | Arthur et al. | 73/819 |
| 4,625,544 | 12/1986 | Yuan et al. | 73/38 |
| 4,627,270 | 12/1986 | Jones | 73/38 |
| 4,631,677 | 12/1986 | Park et al. | 364/422 |
| 4,638,447 | 1/1987 | Odeh | 364/556 |
| 4,643,019 | 2/1987 | Jones | 73/38 |
| 4,648,261 | 3/1987 | Thompson et al. | 73/38 |
| 4,649,737 | 3/1987 | Jones | 73/38 |
| 4,669,299 | 6/1987 | Closmann | 73/38 |
| 4,679,421 | 7/1987 | Barree | 73/38 |
| 4,679,441 | 7/1987 | Johnson et al. | 73/798 |
| 4,710,948 | 12/1987 | Withjack | 378/208 |
| 4,715,212 | 12/1987 | Johanson | 73/38 |
| 4,753,107 | 6/1988 | Reed et al. | 73/38 |
| 4,762,003 | 8/1988 | Cioletti | 73/825 |
| 4,791,822 | 12/1988 | Penny | 73/865 |
| 4,799,382 | 1/1989 | Sprunt et al. | 73/153 |
| 4,807,465 | 2/1989 | Botzolakis et al. | 73/78 |
| 4,825,700 | 5/1989 | Vardoulakis et al. | 73/749 |
| 4,827,761 | 5/1989 | Vinegar et al. | 73/38 |
| 4,845,995 | 7/1989 | Kaste et al. | 73/794 |
| 4,848,145 | 7/1989 | Blaschke et al. | 73/153 |
| 4,856,341 | 8/1989 | Vinegar et al. | 73/798 |
| 4,864,846 | 9/1989 | Jones | 73/38 |
| 4,868,751 | 9/1989 | Dogru et al. | 364/422 |
| 4,884,438 | 12/1989 | Jones et al. | 73/153 |
| 4,885,941 | 12/1989 | Vardoulakis et al. | 73/794 |
| 4,955,237 | 9/1990 | Suzuki et al. | 73/784 |
| 4,957,001 | 9/1990 | Powell | 73/716 |
| 4,961,343 | 10/1990 | Boone | 73/152 |
| 5,018,396 | 5/1991 | Penny | 73/865.6 |
| 5,025,668 | 6/1991 | Sarda et al. | 73/795 |
| 5,025,669 | 6/1991 | Sarda et al. | 73/798 |
| 5,065,421 | 11/1991 | Morineau et al. | 73/38 |

APPARATUSES AND METHODS FOR MEASURING ULTRASONIC VELOCITIES IN MATERIALS

BACKGROUND OF THE INVENTION

1. Field of the Invention

This invention is related to triaxial tests of rock and, in one aspect, to triaxial test apparatuses and methods for low permeability rock, e.g. shales, to determine various properties of the rock such as mechanical strength properties, ultrasonic velocities and elastic properties, e.g. Poisson's ratio, Young's Modulus, bulk modulus, etc., and elasto-plastic properties. In one aspect this invention is directed to triaxial test apparatuses and methods employing ultrasonic transducers to rapidly measure ultrasonic velocities of low permeability rocks during a triaxial test with accurate pore pressure measurements, allowing determination of an ultrasonic velocity-mean effective stress relationships with one test or multiple tests and for other relationships including ultrasonic velocity-mean effective stress-elastic property; and ultrasonic velocity-mean effective stress-elasto plastic property.

2. Description of Related Art

Wellbore stability has been frequently identified as one of the major sources of trouble costs for drilling in shale. In order to minimize wellbore stability related trouble costs, testing programs have been developed to build data bases and generalize the mechanical properties of different shales. Very high quality and useful results have been obtained. However, such test programs are very tedious and require many tests (e.g. 15-20) to quantify the properties for one shale type.

Figure 1:
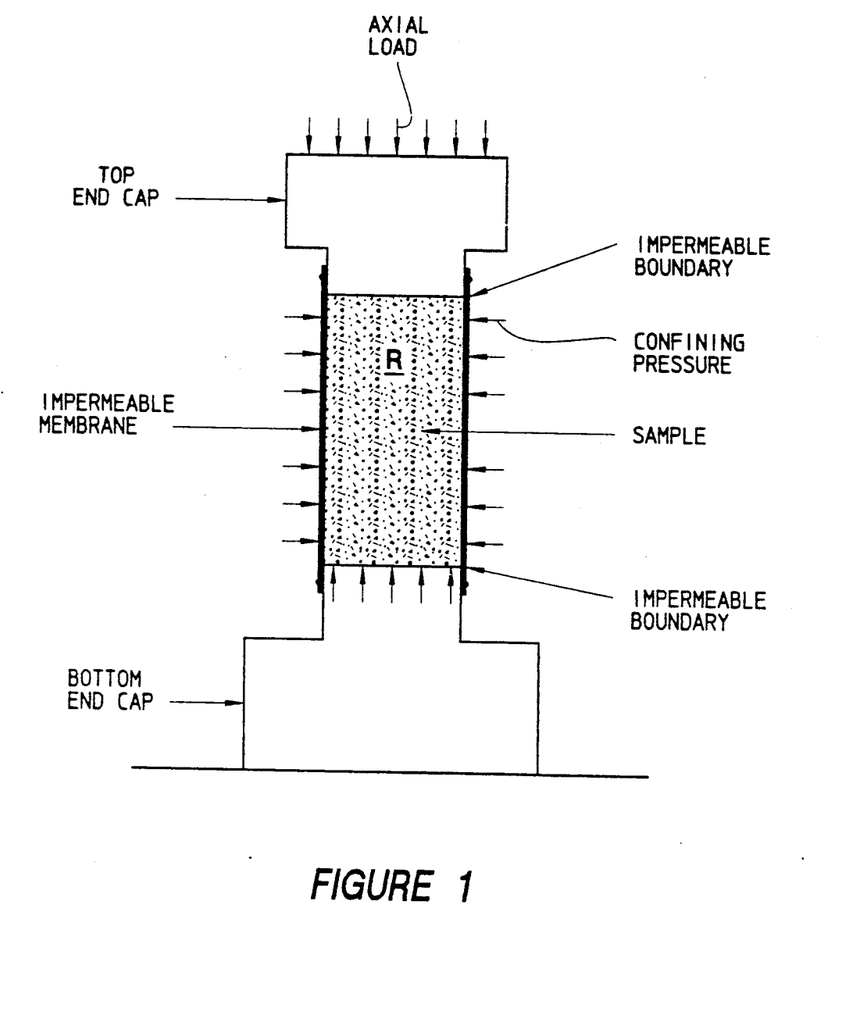
FIG. 1 is a schematic view of a prior art triaxial test apparatus.

FIG. 1 illustrates a conventional triaxial test apparatus for rock testing. The test is performed inside an enclosed hydraulic cell and a confining fluid pumped into the cell provides a confining pressure on a rock sample specimen to be tested. The rock sample is placed on the bottom end cap for support. During the test, hydraulic pressure is applied around the sample to generate an isostatic confining stress and then an axial load (usually via a load piston) is applied to the top end cap to generate a deviatoric (shear) stress. The prior art does not teach monitoring of rock water content during a triaxial test of low permeability rocks. Ultrasonic transducers have been used near opposite sides of a rock sample during tests of it.

Prior art tests have employed different apparatuses and methods to obtain ultrasonic velocity measurements for different rocks. However, the prior art methods yield inaccurate results and require a relatively long time to complete measurements for a low permeability rock, such as shale. The prior art methods use badly disturbed, predried rock samples. The samples then are exposed to deionized water to achieve saturation before testing. It is well known that shales alter their mechanical and chemical reaction properties after they lose much of their water to an external system or gain water from an external water source. The prior art methods do not use the special procedures and equipment described in the applications appended hereto, and therefore, well preserved shale samples are not used and pore pressures and effective stresses are not accurately determined during tests. Applicants are unaware of any prior art disclosing triaxial test apparatuses and methods for low permeability rock, such as shales, which employ ultrasonic transducers to measure ultrasonic velocity during a triaxial test at different effective stress levels.

There has long been a need for triaxial test apparatus and methods for low permeability rock utilizing ultrasonic transducers to measure ultrasonic velocities. There has long been a need for such apparatuses and methods in which a single test of a relatively small amount of a core sample can yield the ultrasonic velocity-mean effective stress ultrasonic velocity-mean effective stress-strength, and ultrasonic velocity-means effective stress-elastic property relationships for a low permeability rock. There has long been a need for triaxial test apparatuses and methods which could effectively, accurately, and rapidly measure ultrasonic velocities while simultaneously measuring pore pressure of an undisturbed low permeability rock sample.

SUMMARY OF THE PRESENT INVENTION

Our invention includes a new design of triaxial test apparatus which includes end caps and test procedures to measure ultrasonic velocities while simultaneously measuring pore pressure in low permeability rocks. The end caps contain an ultrasonic transducer which provides sending or receiving capacity for ultrasonic waves (both p-wave and s-wave).

In one embodiment of a triaxial test apparatus according to the present invention, a rock sample mounting apparatus is provided which has a bottom end cap and a top end cap, each with a flat planar face for mounting below (bottom end cap) or above (top end cap) the flat face of the sample. Within each end cap near the flat face adjacent the rock sample is an ultrasonic transducer. One transducer is a transmitter and one is a receiver (either can receive or send). A pore pressure channel extends from the top surface of the bottom end cap to a pore pressure port or chamber in the bottom end cap. Sample fluid expelled from the rock sample during testing (e.g. water or some other fluid) flows into the pore pressure channel. It is inhibited from flowing out of the top of the channel by the top end cap and, even if some minute amount of fluid would escape from the top face of the sample, one or more impermeable flexible jackets covering the side wall of the sample and extending slightly over the end cap to which it is secured prevents sample fluid from exiting from the top-end-cap-top-face-of-the-rock-sample interface and from the bottom interface also. Sample fluid expelled into the pore pressure channel contacts a pore pressure fluid (preferably a fluid not miscible with the sample fluid) and compresses it somewhat. That compression is sensed by a pore pressure transducer in the pore pressure port and it is conveyed in analog form (a change in voltage) via wiring from the pore pressure transducer to a monitor system (e.g. a computer which can also record data). Deformations in the sample due to the load on it are measured using strain indicators, preferably linear variable differential transformers, for indicating vertical axial deformation and cantilevered strain gauges for indicating radial deformation. In one embodiment, the pore pressure channel and pore pressure port are very small and relatively little sample fluid is expelled from the sample (e.g. a shale) so that the sample-fluid content of the sample changes very little during the test, providing conclusive usable data. In one embodiment utilizing a high pressure fluid generator in communication with the pore pressure port, fluid can be withdrawn from a sample during testing by withdrawing pore pressure fluid from the pore pressure port during testing. In one embodiment, the top end cap also has a pore pressure channel with a port and in which is mounted a pore pressure transducer, the transduce having the associated wiring connectible to an external monitor-recording system. Thus, the fluid content of the sample can be adjusted and controlled during a test, thereby varying and controlling a sample's mean effective stress during testing. The end caps are, preferably, made from high strength material, e.g. hardened steel or titanium.

According to the present invention, a test is provided for defining the relationship between the ultrasonic velocity in a rock and the mean effective stress of the rock. The traveling velocity (v) of ultrasonic waves, both compression (p-wave) and shear (s-wave) waves, through a rock sample is measured by sending waves from one side of the sample and receiving wave information from the other side of the sample. The ultrasonic test is performed during a compression test or at the end of each stage of a multi-stage compression test, e.g. as described in the co-pending application entitled "Test Apparatuses And Methods For Adjusting A Material's Fluid Content And Effective Stresses." The ultrasonic velocities increase with effective mean stress applied on the sample. Consistent correlation between these two parameters (velocity and stress) can be observed.

Appended hereto and included fully herein for all purposes are copies of the following applications, filed on even date herewith, and co-owned with this application:

"Methods And Apparatuses For Measurement Of The Strengths, Pore Pressures, And Mechanical Properties Of Low Permeability Geologic Materials," naming Mr. Ronald P. Steiger as inventor.

"Method For Determining In Situ Shale Strengths, Elastic Properties, Pore Pressures, Formation Stresses And Drilling Fluid Parameters," naming Messrs. Ronald P. Steiger and Peter K. Leung as co-inventors.

"Test Apparatuses And Methods For Adjusting A Material's Fluid Content And Effective Stresses," naming Messrs. Ronald P. Steiger and Peter K. Leung as co-inventors.

"Microaccumulator For Measurement of Fluid Volume Changes Under Pressure," naming Messrs. Ronald P. Steiger, Peter K. Leung, and Rudolf J. Stankovich as co-inventors.

It is, therefore, an object of the present invention to provide new, useful, unique, efficient and nonobvious apparatuses and methods for measuring ultrasonic velocities while measuring pore pressure in low permeability rocks, particularly performing such measurements rapidly and accurately.

A further object of the present invention is the provision of new, useful, unique, efficient and nonobvious apparatuses and methods for determining the ultrasonic velocity - mean effective stress, ultrasonic velocity-mean effective stress-strength, ultrasonic velocity-mean effective stress-elastic property, ultrasonic velocity-mean effective stress-elasto plastic property relationships for a rock in a single test.

The present invention recognizes and addresses the previously-mentioned long-felt needs and provides a satisfactory meeting of those needs in its various possible embodiments. To one of skill in this art who has the benefits of this invention's teachings and disclosures, other and further objects and advantages will be clear, as well as others inherent therein, from the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or additions of further improvements.

DESCRIPTION OF THE DRAWINGS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments.

DESCRIPTION OF EMBODIMENTS PREFERRED AT THE TIME OF FILING FOR THIS PATENT

Referring now to FIG. 1 a typical prior art triaxial test set-up is shown schematically. Mounting apparatus for a rock sample R include a top end cap and a bottom end cap. An impermeable membrane (e.g. a plastic or rubber jacket or jackets) is placed over the sample R. The jacket extends onto each end cap to which it is secured, e.g. by a wire rope, creating impermeable boundaries at each end of the sample R. Appropriate strain indicators are applied to the sample to indicate the extent of deformation of the sample during testing. The bottom end cap rests on a load cell which indicates the amount of axial load applied to the sample R by a load piston (not shown). A confining fluid pumped into a sealed housing (not shown) into which the mounted sample R is placed provides a desired confining pressure on the sample. This pressure is measured by a transducer in the housing.

Figure 2:
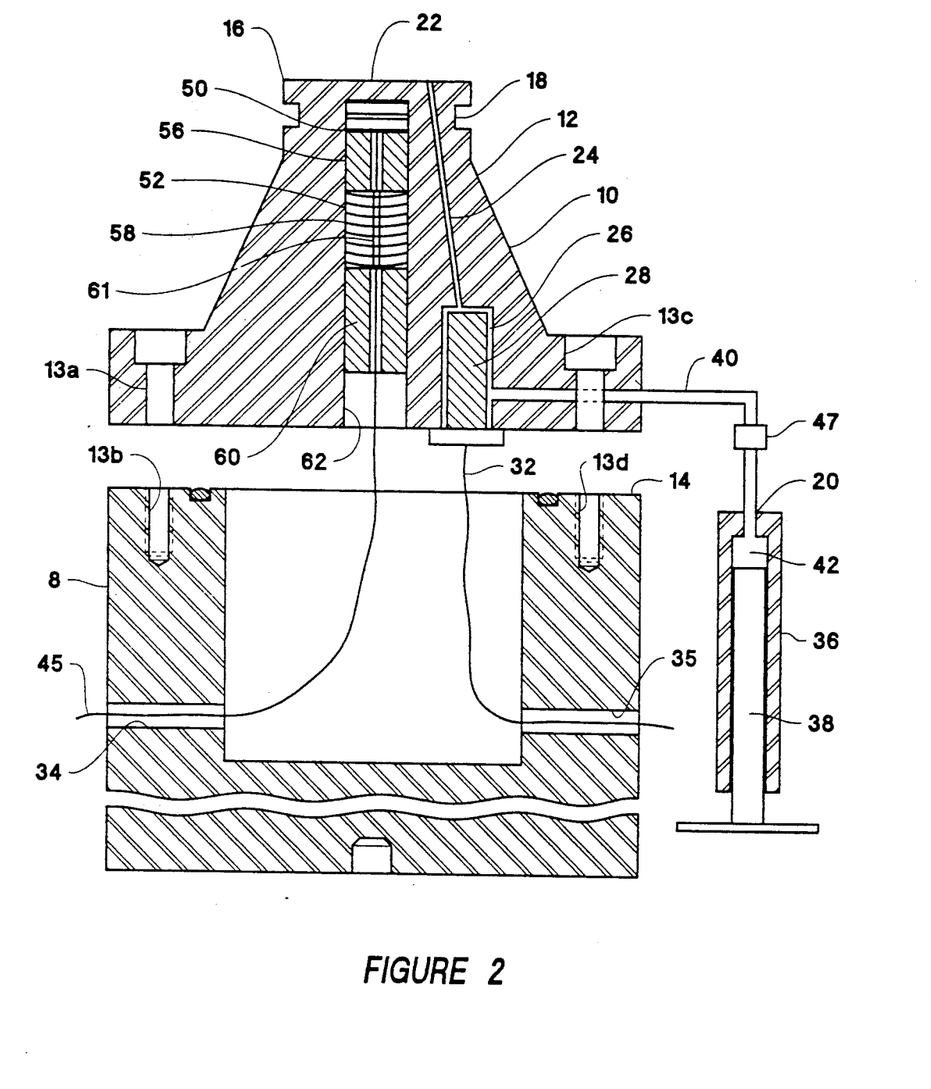
FIG. 2 is a side cross-sectional view of a triaxial test apparatus including end cap and pressure generator according to the present invention.

A test apparatus 8 according to the present invention is shown in FIG. 2 in cross-section, with an end cap 10 and a high pressure generator 20 in communication therewith. The end cap 10 has a top portion 12 and a bottom portion 14 which are bolted together by bolts (not shown) extending through holes 13a, 13b, 13c, and 13d. An apex 16 of the top portion 12 has a groove 18 for receiving a portion of an impermeable flexible jacket or jackets (not shown) for enclosing the side of a rock sample.

A face 22 of the apex 16 is substantially flat for facing up against a flat surface of a rock sample; and it is preferred that the flatness of the face 22 vary only about 0.001 inch per inch of dimensional extent.

From the face 22 extends a pore pressure channel 24 in the end cap 10 which communicates with a pore pressure port 26 in the end cap 10. A pore pressure transducer 28 in the pore pressure port 26 senses changes in the pressure of a pore pressure fluid that fills the pore pressure port and the pore pressure channel. Sensed changes are conveyed via wiring 32 to a recorder or monitor (e.g. a digital data acquisition system or computer, now shown). The wiring 32 exits from the bottom portion 14 of the end cap 10 via a hole 35.

Sample fluid expelled from a rock sample mounted above the end cap 10 will move into the pore pressure channel 24 compressing a pore pressure fluid in the pore pressure channel 24 and in the pore pressure port 26. Preferably this pore pressure fluid is not miscible with the sample fluid; does not react with the sample or the sample fluid; is inert; and does not wet the sample. For example, if the sample fluid is water or oil, mercury is a preferred pore pressure fluid.

The high pressure generator 20 has a hollow body 36, preferably made from high strength material such as hardened steel or titanium, in which is movably, adjustably and sealingly mounted a piston 38. Pore pressure fluid fills a line 40 in communication with the pore pressure port 26 and an interior space 42 of the hollow body 36. A valve 47 controls flow in the line 40. By moving the piston 38 outwardly, thereby increasing the volume of the interior space 42 that can receive pore pressure fluid, more sample fluid can be expelled from a rock sample mounted to the end cap 10. This is useful if it is desired to remove sample fluid from a rock sample during a test to change the sample's water content and to hereby change the sample's mean effective stress.

It is preferred that the pore pressure channel and pore pressure port be very small in volume so that the amount of sample fluid that is expelled during a test is also small. In this way the variance in the fluid content of the sample during a test is negligible; i.e., the fluid content of the sample remains almost constant so that good conclusive data can be obtained.

An ultrasonic transducer 50 is disposed in a recess 52 in the top portion 12 of the end cap 10. Preferably, the ultrasonic transducer 50 is disposed near the face 22 of the apex 16. Wiring 45 extends from the end cap through a hole 34 for interfacing with a monitor/recording system (e.g. a computer). A nylon spacer 56 is disposed between the transducer 50 and spring washers 58. A threaded nut 60 which is threadedly received in a threaded portion 62 of the recess 52. The wiring 54 extends through holes 64 in the washers 58 and a hole 61 in the washers 58.

Figure 3:
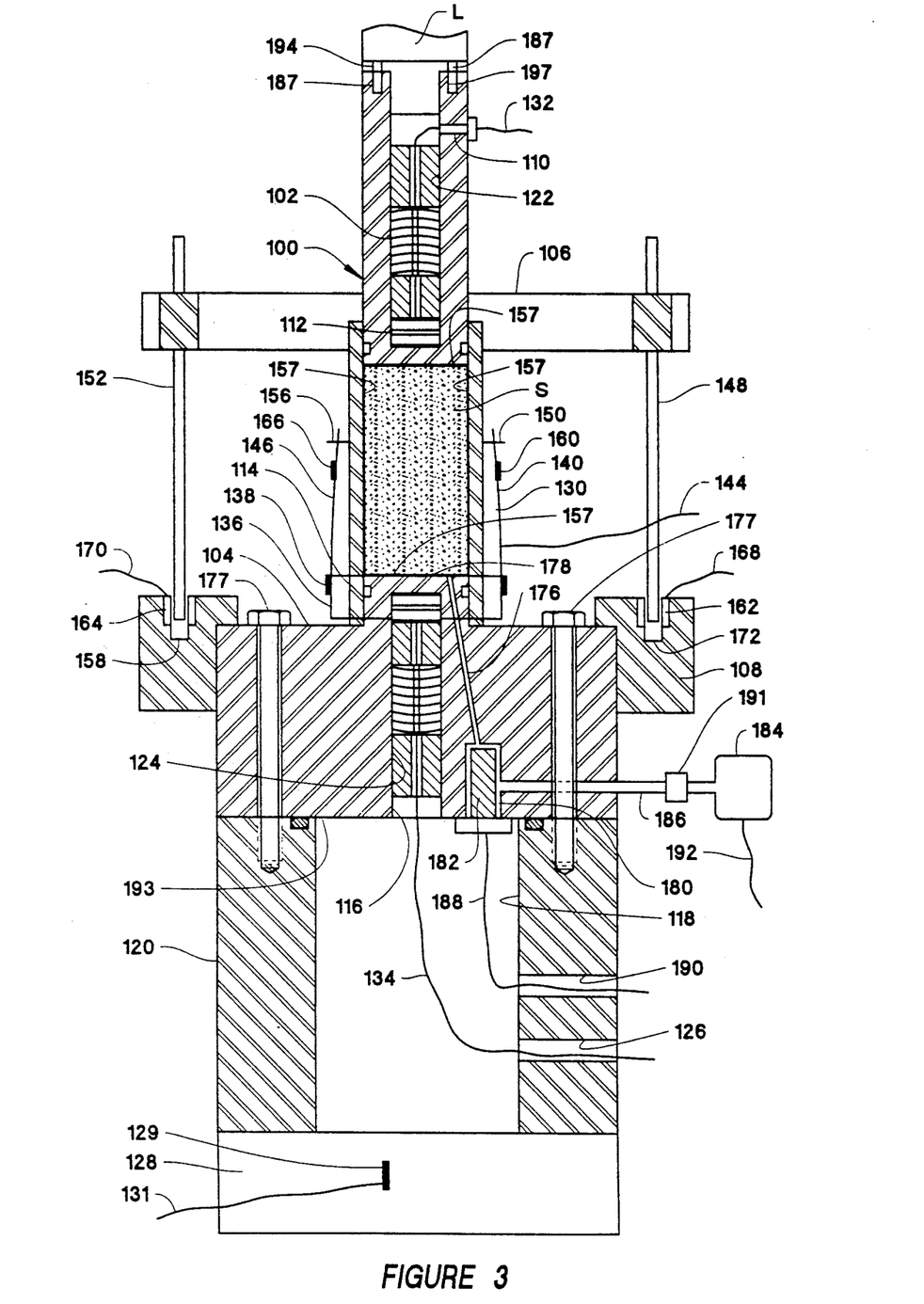
FIG. 3 is a side cross-sectional view of a triaxial test apparatus according to the present invention.

FIG. 3 illustrates, partially schematically, a test apparatus 100 according to the present invention which has a top end cap 102 and a bottom end cap 104 mounted to a rock sample specimen S to be tested in a triaxial test cell (not shown). A holder 106 is secured to the top end cap 102 and a collar 108 is secured to the bottom end cap 104. The bottom end cap 104 is bolted with bolts 177 to a bottom base 120.

Each end cap 102, 104 has an ultrasonic transducer 112, 114 respectively, disposed therein in recesses 122, 124, respectively. These transducers and their related apparatus are like the transducer 50 of FIG. 2. Wiring 132, 134 extends from the transducers for interfacing with a monitoring system (e.g. a computer). The wiring 132 extends through a hole 110 in the top end cap 102 and the wiring 134 extends through a hole 116 in the bottom end cap 104, through a channel 118 in the bottom base 120, and out through a sealed lead-through 126 in the base 120. The base 120 rests on a typical load cell 128 with a strain gauge 129 and its associated wiring 131. A top plug 194 closes off the recess 122. Bolts 187 bolt the plug 194 to the top end cap's body.

Cantilevered strain gauges 130 and 136 (more may be used, e.g. four or more spaced around the sample) are mounted to a mounting ring 138 which is secured about the end cap 104. Beams 40 and 146 extend upwardly from the ring 138 and pins 150 and 156 contact an impermeable flexible jacket 142 (or jackets) that surround the side wall of the sample S. Gauges 160 and 166 on the beams 140 and 146 sense radial deformation of the sample S during compressive loading by a load piston L. Via wiring 144 sensed changes are conveyed to a monitoring system (e.g. a computer).

To sense changes in axial (vertical) deformation of the sample, it is preferred, although not necessary, that linear variable differential transformers (LVDT's) be used because of their accuracy and sensitivity. The holder 106 is mounted to the top end cap 102. Secured to the holder 106 are LVDT rods 148 and 152 which extend into recesses 172 and 158 in the collar 108. The rods 148 and 152 are movable within, respectively, coils 162 and 164 disposed in the collar 108. Movement of the rods due to axial deformation of the sample S changes the voltage of the coils and this change is conveyed to a monitoring system wiring 168 and 170.

A pore pressure channel 176 extends from a top face 178 of the bottom end cap 104 and into a pore pressure port 180 in which is disposed a pore pressure transducer 182 for sensing changes in a pore pressure fluid in the port 180 due to sample fluid being expelled from the sample S during testing or due to pressure changes caused by a microaccumulator 184 which is in communication with the pore pressure port 180 via a line 186. A valve 191 controls flow in line 186. Wiring 188 extends from the pore pressure transducer through a sealed lead-through 190 in the base 120 for interfacing with a monitor system for indicating and recording changes in the pressure of the pore pressure fluid. Alternatively, the top end cap could be made with a pore pressure channel and port and a pore pressure transducer to measure pore pressure from a top surface of the sample.

As shown in FIG. 3, a screen 157 encloses the sample 5. This screen has three components spot welded together—a 300 mesh outer screen; a 100 mesh middle screen; and a 300 mesh inner screen. As disclosed in the co-pending application co-owned with the present application entitled "Test Apparatuses and Methods For Adjusting A Material's Fluid Content And Effective Stresses," flow of sample fluid expelled from a sample may be facilitated by providing such a wire screen mesh or screens around the sample prior to installing flexible jackets on it. The screens create a flow path whereas the flexible jackets alone impede flow. By using multiple screens secured together, e.g. by spot welding, fine mesh screens to the outside, i.e. facing the sample and the flexible jacket, can inhibit the sample or the jacket moving into the mesh while an inner coarser mesh screen facilitates fluid flow down the sample and into a pore pressure channel.

It is preferred that the microaccumulator 184 be of the design disclosed in the co-pending application entitled "Microaccumulator For Measurement Of Fluid Volume Changes Under Pressure," filed on even date herewith and a copy of which is submitted herewith and incorporated fully herein for all purposes. Wiring 192 extends from the microaccumulator 184 for interface with a monitoring system, e.g. a computer, which may also control the microaccumulator.

In one method according to the present invention a well preserved and undisturbed rock sample cored from a wellbore is mounted with end caps according to this invention. Then, a constant isostatic confining pressure, p, is applied on the rock sample in a triaxial cell. The sample's pore pressure is allowed to equilibrate with the cell's confining pressure. Pore pressure, u, is measured by a pore pressure sensor (e.g. pore pressure transducer 28, FIG. 2) in the pore pressure port and the mean effective (confining) stress, p', is defined as (p-u). The test is performed in multi-stages. In each stage of the test, a small amount of water is withdrawn from the sample by adjusting the high pressure generator (e.g. item 20, FIG. 2) outward or by adjusting a microaccumulator. This decreases the sample's water content by steps, thereby increasing its mean effective stress by steps, since lowering the sample's water content lowers its pore pressure. When one stage is completed and the water content has been reduced, time is again allowed for the sample's pore pressure to equilibrate with the confining pressure of the confining fluid within the test cell. Once a substantially constant sample pore pressure is achieved, the next step of the loading is commenced. By calculating the sample water content and mean effective stress for each stage of the test, their relationships can be accurately defined in one multi-stage test.

Figure 4:
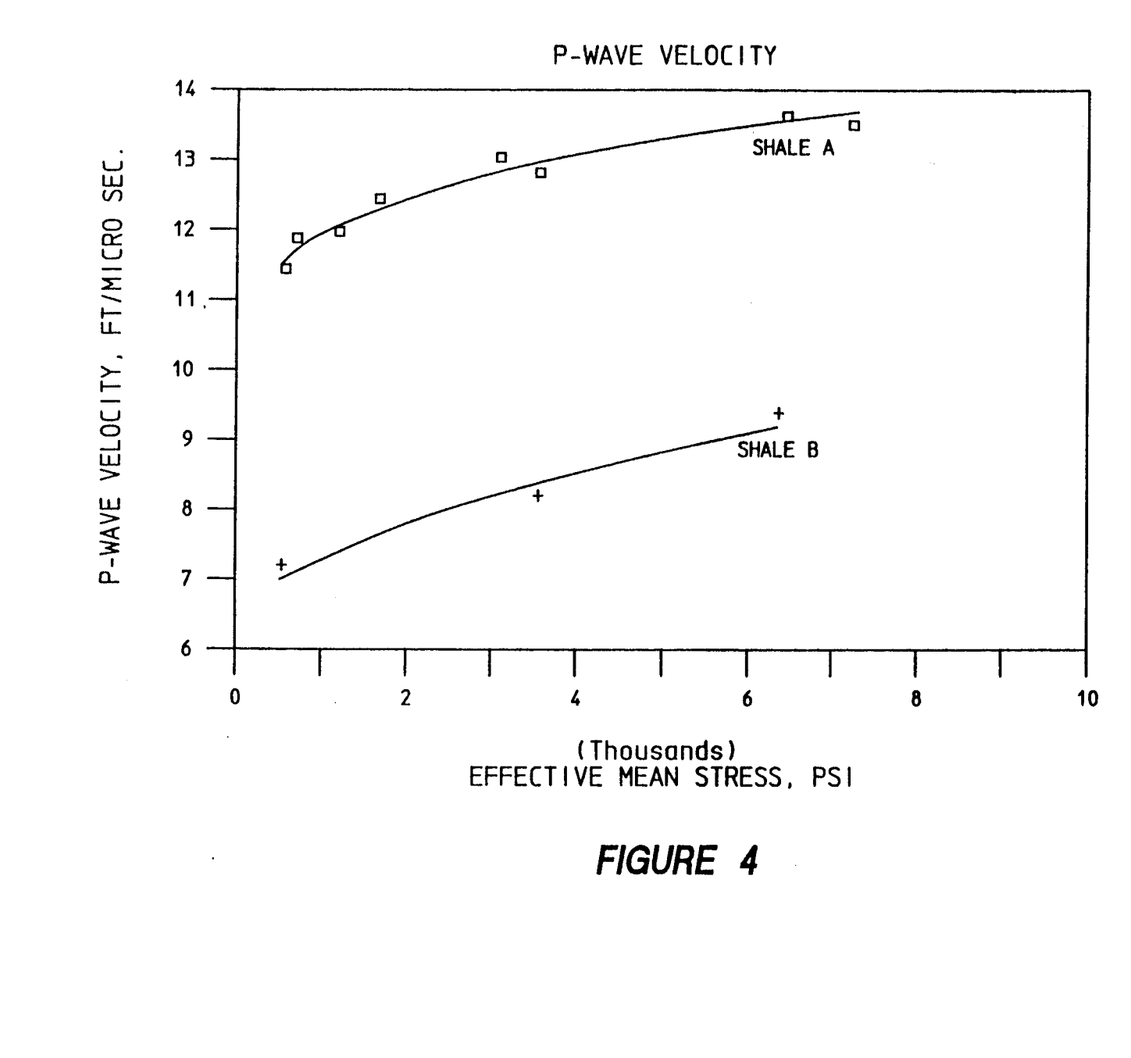
FIG. 4 presents a graph of a rock's ultrasonic velocity (vertical axis) versus its mean effective stress (horizontal axis).

The traveling velocity (v) of ultrasonic waves, both compression (p-wave) and shear (s-wave) waves, through the rock sample is measured by sending waves from one side of the sample and receiving wave information from the other side of the sample. The ultrasonic test is performed at the end of each stage of the compression test described above. The ultrasonic velocities increase with mean effective stress applied on the sample. FIG. 4 presents ultrasonic data for two types of shales [shale A was a hard (strong) shale; i.e. a shale with a relatively low surface area; shale B was a weak (soft) shale, i.e., a shale which had a relatively high surface area] as a function of mean effective stress, p'. Consistent correlation between these two parameters can be observed.

The present invention includes within its scope apparatuses (and methods using them) in which no high pressure generator or microaccumulator is used, but then the sample's fluid content cannot be adjusted or changed during the test, e.g., multi-stage step-wise tests on one sample are not done.

Figure 5:
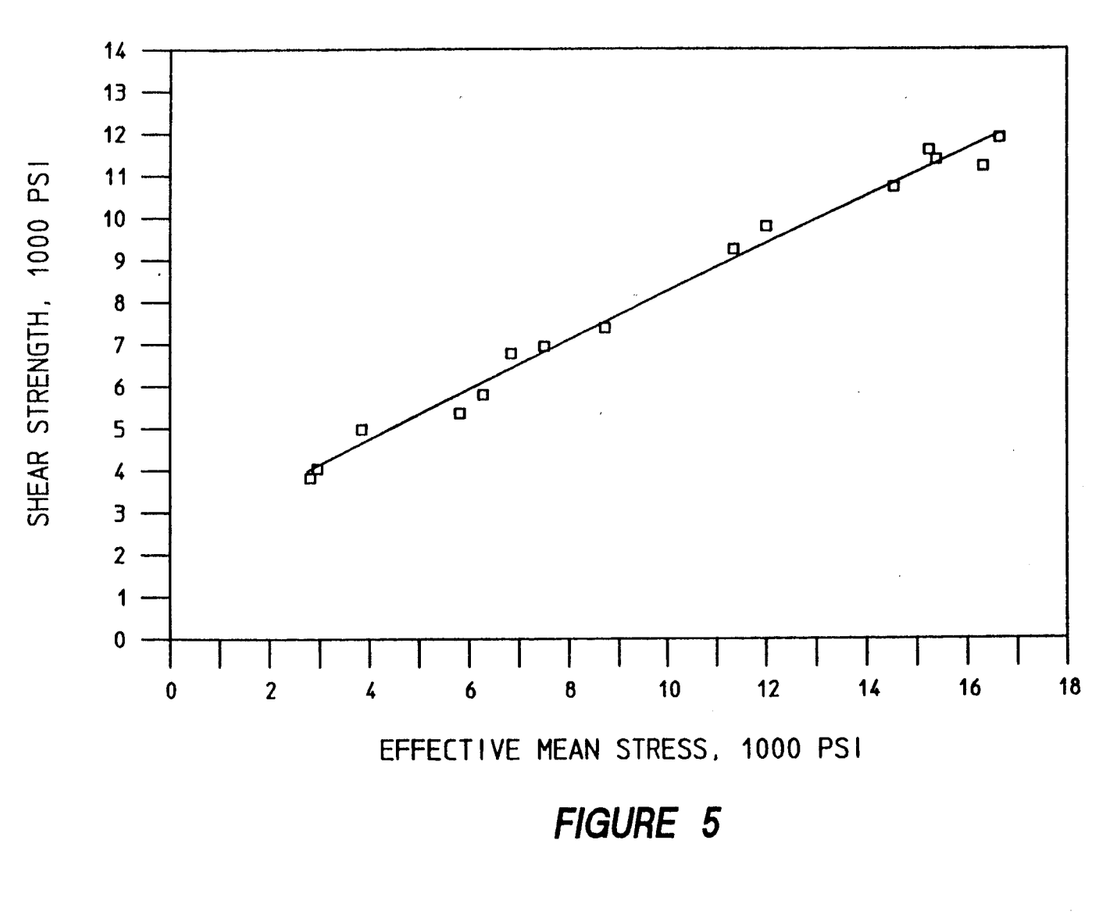
FIG. 5 presents a graph of shale strength (vertical axis) versus mean effective stress (horizontal axis).

The data presented in FIG. 5 was obtained with a triaxial test setup of the type shown in FIGS. 2 and 3, but without a high pressure generator or microaccumulator for water content adjustment. Therefore, each curve (one type of rock) represents the results of several tests. With the apparatus of FIGS. 2 or 3, this correlation for one rock type can be generated by one multi-stage test.

FIG. 5 presents a graph of shale strength versus mean effective stress. This data was developed using the apparatuses and methods described in the copending application entitled "Methods And Apparatuses For Measurement Of The Strengths, Pore Pressures, And Mechanical Properties Of Low Permeability Geologic Materials," but without changing sample water content during testing. Several tests were done on uniform cores with different water contents. However, with apparatus and methods according to this invention, only one multi-stage test is needed.

Figure 6:
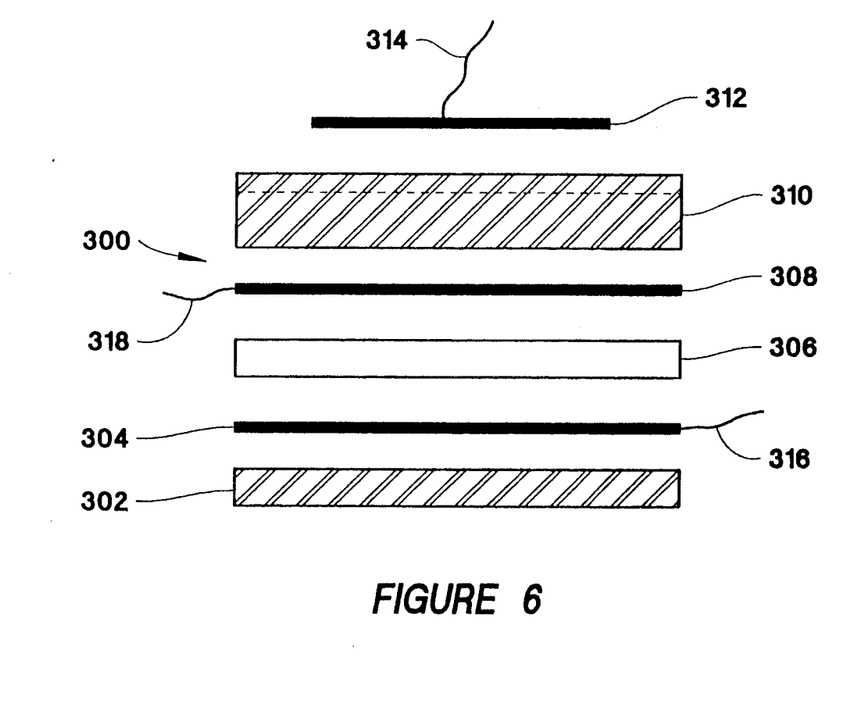
FIG. 6 is a side cross-sectional view of an ultrasonic transducer according to the present invention.

FIG. 6 shows an exploded side cross sectional view of an ultrasonic transducer according to the present invention having a shear wave crystal 302 (preferably about 1/32 inch thick); a piece of shim stock wiring contact 304 (copper); a piece of insulation 306 (e.g. ceramic) (preferably about 1/32 inch thick; a piece of shim stock wiring contact 308; a p-wave crystal 310 (preferably about 1/16 inch thick); and a wiring contact 312 (copper) (preferably about 0.001 inch thick) with wiring 314. Wiring 318 extends from the shim 308 and wiring 316 extends from the shim 304.

In one embodiment of a method for determining an ultrasonic velocity-mean effective stress envelope for a material according to the present invention includes applying a first confining stress to the material, measuring and recording the material's pore pressure at a first confining stress, measuring the ultrasonic velocity through the material at the first confining stress level, calculating a value for the mean effective stress of the material at the first confining stress level, repeating the previous steps at multiple confining stress levels and obtaining a value for the mean effective stress at each level, plotting the value thus obtained on a graph, and determining a curve that fits the plotted points.

One embodiment of a method for determining an ultrasonic velocity-mean effective stress-strength envelope for a material according to this invention includes applying a first confining stress to the material, measuring and recording the material's pore pressure at a first confining stress, measuring the ultrasonic velocity through the material at the first confining stress level, calculating a value for the mean effective stress of the material at the first confining stress level, loading the sample to near its shear failure level, measuring the load to determine the strength at that load, repeating the previous steps at multiple confining stress levels and obtaining values for the mean effective stress and strength at each level, plotting the values thus obtained on a three-axis graph, and determining a curve that fits the plotted points.

One embodiment of a method for determining an ultrasonic velocity-mean effective stress-elastic property envelope for a material according to this invention includes applying a first confining stress to the material, measuring and recording the material's pore pressure at a first confining stress, measuring the ultrasonic velocity through the material at the first confining stress level, calculating a value for the mean effective stress of the material at the first confining stress level, loading the sample to near its shear failure level, measuring the load to determine the value of the elastic property at that load, repeating the previous steps at multiple confining stress levels and obtaining a value for the mean effective stress and the elastic property at each level, plotting the values thus obtained on a three-axis graph, and determining a curve that fits the plotted points.

One embodiment of a method for determining an ultrasonic velocity-mean effective stress-elastoplastic property envelope for a material according to this invention includes applying a first confining stress to the material, measuring and recording the material's pore pressure at a first confining stress, measuring the ultrasonic velocity through the material at the first confining stress level, calculating a value for the mean effective stress of the material at the first confining stress level, loading the sample to near its shear failure level, measuring the load and determining the value of the elastoplastic property at that load, repeating the previous steps at multiple confining stress levels and obtaining values for the mean effective stress and the elastoplastic property at each level, plotting the values thus obtained on a three-axis graph, and determining a curve that fits the plotted points.

In conclusion, therefore, it is seen that the present invention and the embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

What is claimed is:

1. A method for determining an ultrasonic velocity-mean effective stress-elastoplastic property envelope for a preserved core sample of material, the method comprising
   (a) applying a first confining stress to the sample, the material having a pore pressure, a mean effective stress, an elastoplastic property and values thereof,
   (b) measuring and recording the material's pore pressure at a first confining stress,
   (c) measuring an ultrasonic velocity through the material at the first confining stress level,
   (d) calculating a value for the mean effective stress of the material at the first confining stress level,
   (e) continuously measuring strain of the sample,
   (f) loading the sample to near its shear failure level to obtain an elastoplastic property value,
   (g) measuring load on the sample and strain of the sample and determining the value of the elastoplastic property at the load near shear failure,
   (h) repeat the previous steps (a)–(g) at multiple confining stress levels and obtain values for the mean effective stress and the elastoplastic property at each level,
   plot the values thus obtained for mean effective stress, elastoplastic property, and ultrasonic velocity on a three-axis graph, and
   determine a curve that fits the plotted points.

2. The method of claim 1 wherein the material is shale.

3. The method of claim 1 wherein the load is applied continuously and pore pressure and ultrasonic velocity are measured and recorded continuously.

4. The method of claim 1 wherein the water content of the sample is changed during the measuring and recording steps so that the measuring steps occur at different sample strength levels.

5. The method of claim 1 wherein the elastoplastic property of the material is its strength.

6. The method of claim 1 wherein a sample of the material is prepared and mounted by mounting a pore pressure transducer in a pore pressure chamber in a bottom end cap of a triaxial test apparatus, the sample having a top and a bottom, the pore pressure chamber in fluid communication with a pore pressure channel extending to a surface of the end cap for disposition adjacent the sample to be tested, the pore pressure channel for receiving sample fluid expelled from the sample during testing, evacuating substantially all the air from the pore pressure channel and from the pore pressure chamber and then filling them with an inert fluid immiscible with the sample fluid, and in a sealed chamber, applying a screen member around the sample to facilitate the flow of sample fluid into the pore pressure channel, applying a flexible impermeable jacket to the sample, other than to its ends, and applying the bottom end cap to the bottom of the sample and a top end cap to the top end of the sample, each end cap having an ultrasonic transducer therein and transducer wiring leading therefrom connected to an exterior system for monitoring and recording signals from the sample, the method further comprising
   placing the sample in a confinement vessel of a triaxial test apparatus and sealing the vessel shut,
   isostatically loading the sample by introducing a confining fluid under pressure into the confinement vessel to provide a constant confining pressure on the sample,
   interconnecting the pore pressure transducer and the ultrasonic transducers with the exterior system,
   allowing the sample's pore pressure to equilibrate with the pressure of the confining fluid,
   applying a load piston to the top end cap to apply a known load on the sample, the piston sealingly extending through the confinement vessel to contact the sample,
   measuring and recording pore pressure of the sample continuously during the test, and
   measuring and recording ultrasonic velocity of ultrasonic waves transmitted through the sample by one ultrasonic transducer and received by the other continuously during the test.

7. The method of claim 6 including applying strain indicators to the sample before sealing the vessel and connecting the strain indicators to the exterior system and measuring and recording axial and radial strain of the sample continuously.

8. The method of claim 7 including changing the pressure of the inert fluid by adjusting a high pressure generator in fluid communication with the pore pressure channel and pore pressure port, thereby changing pressure on the sample, and repeating the steps of the test method at a new sample pressure level.

* * * * *